United States Patent [19]

Akram et al.

[11] Patent Number: 6,139,853
[45] Date of Patent: Oct. 31, 2000

[54] HAIR COLORANTS AND AN APPLICATION MIXTURE FOR COLORING HUMAN HAIR

[75] Inventors: Mustafa Akram, Hamburg; Wolfgang Wolff, Bargteheide; Sandra Rohweder, Hamburg; Stephan Schwartz, Wedel, all of Germany

[73] Assignee: Hans Schwarzkopf GmbH & Co. KG, Hamburg, Germany

[21] Appl. No.: 09/101,252

[22] PCT Filed: Dec. 19, 1996

[86] PCT No.: PCT/EP96/05714

§ 371 Date: Jul. 6, 1998

§ 102(e) Date: Jul. 6, 1998

[87] PCT Pub. No.: WO97/25017

PCT Pub. Date: Jul. 17, 1997

[30] Foreign Application Priority Data

Jan. 5, 1996 [DE] Germany .............. 196 00 221

[51] Int. Cl.[7] .............. A61K 7/00; A61K 7/13; A61K 7/135; A61K 7/06; A61K 9/00
[52] U.S. Cl. .............. 424/401; 8/408; 424/62; 424/70.1; 424/400; 424/489; 424/502
[58] Field of Search .............. 424/401, 70.1, 424/62, 489, 502, 400; 8/408

[56] References Cited

U.S. PATENT DOCUMENTS

| | | | |
|---|---|---|---|
| 4,183,366 | 1/1980 | Bartuska et al. | 132/7 |
| 4,275,055 | 6/1981 | Nachtigal et al. | 424/70 |
| 4,658,839 | 4/1987 | Dallal et al. | 132/7 |
| 4,808,189 | 2/1989 | Oishi et al. | 8/408 |
| 4,898,595 | 2/1990 | Fridd et al. | 8/405 |
| 5,102,655 | 4/1992 | Yoshihara et al. | 424/62 |
| 5,525,123 | 6/1996 | Lorenz et al. | 8/408 |

FOREIGN PATENT DOCUMENTS

| | | |
|---|---|---|
| 900 219 | 1/1985 | Belgium . |
| 1 583 606 | 10/1969 | France . |
| 2 510 401 | 2/1983 | France . |
| 38 29 102 | 8/1989 | Germany . |
| 42 33 874 | 4/1994 | Germany . |
| 2 190 104 | 11/1987 | United Kingdom . |

*Primary Examiner*—Shelley A. Dodson
*Assistant Examiner*—Marina Lamm
*Attorney, Agent, or Firm*—Wayne C. Jaeschke; Real J. Grandmaison; Glenn E. J. Murphy

[57] ABSTRACT

A solid hair colorant composition in powder or granular form containing from 1 to 10% by weight of at least one oxidation dye precursor, from 10 to 35% by weight of an oxidizing agent, from 3 to 25% by weight of a substantive plant dye or 25 to 70% by weight of henna neutral, and optionally conventional cosmetic additives.

12 Claims, No Drawings

HAIR COLORANTS AND AN APPLICATION MIXTURE FOR COLORING HUMAN HAIR

BACKGROUND OF THE INVENTION

This invention relates to solid hair colorants and to application mixtures prepared therefrom for coloring hair.

1. Field of the Invention

The use of plant dyes in hair colorants has been known for some time. Fairly recent developments in this field are disclosed, for example, in FR 1 583 606, in BE 900219, in GB 2,190,104 and in DE 38 29 102. DE-A1 42 33 874 relates to hair tinting formulations in granular form which contain plant dyes in combination with synthetic substantive dyes.

2. Disussion of Related Art

Unfortunately, these known colorants based on plant dyes have the disadvantage that their ability to cover grey hair is very often unsatisfactory.

On the other hand, coloring with so-called oxidation dyes is known to the expert. In this case, coloring is achieved by the penetration of oxidation dye precursors into the hair where they react either together or with other oxidation dye precursors in the presence of an oxidizing agent to form the actual dyes. Excellent durable colors, which also cover grey satisfactorily, are obtained in this way. In view of the oxidizing agents used, however, unwanted impairment of the hair structure or even hair damage can occur, particularly in the event of fairly frequent application.

Accordingly, the problem addressed by the present invention was to provide hair colorants with which grey could be safely covered in the coloring of hair without any adverse effect on the hair structure.

Description of the Invention

It has now surprisingly been found that the required coloring effect and covering of grey hair can be obtained without any adverse effect on the hair structure by colorants based on oxidation dye precursors providing the colorants also contain a substantive plant dye or the plant product henna neutral.

Accordingly, the present invention relates to solid hair colorants in powder or granular form containing at least one oxidation dye precursor, an oxidizing agent and typical cosmetic additives, characterized in that they contain at least one substantive plant dye or henna neutral.

Although the products according to the invention are particularly suitable for coloring hair, they may also be used in principle for other coloring applications, for example for coloring textile fibers or wool.

The hair colorants according to the invention are present in powder or granular form. They contain an oxidation dye precursor as a first compulsory component.

In one embodiment of the invention, the hair colorants according to the invention contain only one oxidation dye precursor of the primary intermediate type.

Examples of primary intermediates suitable for in accordance with the invention are primary aromatic or heteroaromatic amines containing another functional group in the p-position, such as for example p-phenylenediamine, p-toluylenediamine, p-aminophenol, 3-methyl-4-aminophenol, 2-(2-hydroxy-ethyl)-1,4-aminobenzene, 2,4,5,6-tetraaminopyrimidine, 2-hydroxy-4,5,6-triaminopyrimidine, 2,5-diaminopyridine and derivatives thereof. According to the invention, other compounds of the type mentioned additionally containing one or more functional groups, such as OH groups, $NH_2$ groups, NHR groups or $NRIR^2$ groups, where R, $R^1$ and $R^2$ independently of one another represent optionally substituted $C_{1-4}$ alkyl groups, are also suitable.

However, the colorants according to the invention preferably also contain at least one secondary intermediate. According to the invention, colorants containing more than one primary intermediate and more than one secondary intermediate may also be preferred.

According to the invention, preferred secondary intermediates are α-naphthol, resorcinol, 4-chlororesorcinol, 2-methyl resorcinol, m-aminophenol, m-phenylenediamine, m-toluylenediamine, 1,5- and 1,7-dihydroxynaphthalene, 5-amino-2-rnethylphenol, 6-amino-2-methylphenol or derivatives of the compounds mentioned. These secondary intermediates may be used either on their own or in combination with other secondary intermediates of the type just mentioned or in combination with other secondary intermediates known to the expert.

According to the invention, primary and secondary intermediates containing amino groups may also be used in the form of their salts, particularly hydrochlorides and sulfates.

Another compulsory component of the colorants according to the invention is the oxidizing agent.

Suitable oxidizing agents are addition compounds of hydrogen peroxide with urea, melamine, potassium and sodium perborate and mixtures of such hydrogen peroxide addition compounds with potassium, sodium or ammonium peroxodisulfate.

According to the invention, potassium perborate and, in particular, sodium perborate—either individually or in combination with other oxidizing agents—are preferred.

In one embodiment of the invention, the hair colorants additionally contain a substantive plant dye. The substantive plant dye is normally present in the form of a powder obtainable by grinding and subsequent sieving of various plant parts, such as stems, flowers/blossom, leaves, roots, fruit and seeds. According to the invention, suitable starting materials are, for example, camomile, small camomile flowers, hibiscus flowers, safflowers and sunflowers, the leaves of the walnut tree, the henna, the indigo plant, the sumach and the elder, rubiaceae roots (dyer's madder, woodruff, bedstraw), curcuma roots, lotus roots and rhubarb roots, red sandal, campeachy, Brazil and Pernambuco woods, alder, strawberry tree and sumach bark, oleander seeds, saffron blossom stigmata, curcuma and bloodwort rootstocks, sloe plums, broom branches and whole plants of weld, lichens and golden rod.

Particularly preferred plant dyes are the henna dyes. Red henna consists of the dried powdered leaves of the plants *Lawsonia alba, Lawsonia spinosa* and/or *Lawsonia inermis*. So-called henna black comes from the leaves of dyer's woad (*Isatis tinctoria*) and is used in mixtures with Lawsonia henna to obtain darker shades of red.

Other preferred plant dyes emanate from walnut shells, indigo, camomile, logwood and black alder bark.

Henna neutral may also be used as an alternative to the plant dyes mentioned above.

Henna neutral consists of the powdered leaves and/or powdered bark of *Cassia auriculata*. However, a corresponding product can also be produced from the leaves of the lotus tree.

Although only one plant dye or henna neutral need be present in the hair colorants according to the invention, the invention also encompasses hair colorants which contain both these components.

The hair colorants according to the invention may also contain synthetic substantive dyes as an optional component, more particularly for nuancing the color.

According to the invention, preferred synthetic substantive dyes are 4-hydroxypropylaniino-3-nitrophenol, HC Red No. 3, N,N'-bis-(2-hydroxyethyl)-2-nitro-p-phenylenediamine, HC Blue No. 2, HC Yellow No. 2, HC Yellow No. 12, HC Blue No. 12 and 2-amino-6-chloro-4-nitrophenol.

The hair colorants according to the invention preferably contain the oxidation dye precursors in quantities of 1 to 10% by weight, based on the solid hair colorant as a whole.

The hair colorants according to the invention preferably contain the oxidizing agents, in quantities of 10 to 35% by weight, again based on the solid hair colorant as a whole.

The content of powder-form dye-containing plant parts in the hair colorants according to the invention may be from 3 to 25% by weight. Quantities of 5 to 25% by weight are preferred, quantities of 5 to 15% by weight—again based on the solid hair colorant as a whole—being particularly preferred.

The content of henna neutral in the corresponding embodiments of the invention is at least 25% by weight, based on the solid hair colorant as a whole. However, the percentage content of henna neutral should not exceed 70% by weight. A preferred range for the henna neutral content is from 40 to 65% by weight and, more particularly, from 50 to 60% by weight.

If the hair colorant according to the invention is present in powder form, unwanted dust emission can occur according to the nature of the individual components. This is problematical not only in regard to dosage, but also for example in regard to the working conditions in hair salons.

In one preferred embodiment, therefore, hair colorants according to the invention may be subjected to a special dust-binding treatment.

This is preferably done by spraying on an inert organic compound. The compound in question may be liquid at room temperature or even solid at room temperature providing it can be liquefied by heating to moderately high temperatures. Solid compounds with melting points below 50° C. will normally be used.

To bind (Just, the inert organic substance is preferably sprayed onto the powder-form hair colorant.

Preferred dust binding agents are paraffins, vegetable, animal and synthetic oils and low-melting waxes. Other suitable components are, for example, triglycerides and fatty alcohols. Particularly preferred dust binding agents are paraffins oils, paraffins with melting points in the range from 40° C. to 50° C., polysiloxanes, such as dimethyl polysiloxane, caprylic/capric acid triglyceride, octyl dodecanol and beeswax.

The percentage content of oils or waxes in the hair colorants according to the invention may be between 1 and 30% by weight and, more particularly, is between 7 and 15% by weight, based on the overall composition of the hair colorant.

The hair colorants according to the invention may additionally contain as thickeners guar flour, sodium alginate, gum arabic, guar or caruba gum, pectins, cellulose derivatives, such as methyl cellulose and hydroxymethyl cellulose, hydroxypropyl methyl cellulose and carboxymethyl cellulose, and various polymers, more particularly acrylic acid derivatives. However, inorganic thickeners, such as bentonite and/or silica, may also be used. These thickeners are present in quantities of preferably 0.1 to 5% by weight and, more preferably, 0.5 to 3% by weight, based on the total weight of the hair colorant.

The hair colorants may additionally contain cationic and amphoteric polymers, film-forming anionic and nonionic polymers and also surfactants or mixtures thereof in quantities of—in each case—0.1 to 5% by weight.

Preferred surfactants are soaps, alkyl benzenesulfonates, alkyl naphthalene sulfonates, fatty alcohol sulfates or ether sulfates or sulfonates, quaternary ammonium compounds, fatty acid diethanolamides, polyethoxylated or polyglycerized alkylphenols. The surfactants are present in the hair colorant according to the invention in quantities of 0.1 to 25% by weight and preferably in quantities of 0.1 to 15% by weight, based on the total weight of the colorant.

Finally, any other additives conventionally used in hair colorants, such as in particular penetration agents, sequesterants, antioxidants, buffers and perfumes, may be added to the hair colorants according to the invention.

The present invention also relates to a process for the production of a hair colorant in powder or granular form, in which the oxidation dye precursor, the oxidizing agent, the plant dye and/or the henna neutral are thoroughly mixed, optionally in the presence of additives typically encountered in hair colorants, an inert organic compound optionally liquefied by heating is sprayed onto the powder mixture obtained with continuous agitation and the powder mixture is optionally converted into granular form.

A coloring paste hereinafter referred to as the application mixture is prepared from the hair colorants according to the invention immediately before use by adding corresponding quantities of water.

Preferred application mixtures consist of 15 to 25% by weight of a colorant according to the invention and 75 to 85% by weight of water. They are normally adjusted to a pH of 5.0 to 12.0 by corresponding addition of acids or bases which, in one preferred embodiment, are already present in the colorant. Organic or inorganic acids, hydroxides, alkali metal or alkaline earth metal carbonates or alkali metal silicates may be used for the pH adjustment.

The application mixture may be applied both to wet hair and to dry hair. According to the invention, it is preferably applied to dry hair.

EXAMPLES

1. Application of Hair Colorants According to the Invention

An application mixture of 80 g of hair colorant according to the invention and 320 ml of hot water was prepared in the form of a spreadable paste. The hair coloring paste obtained was immediately applied quickly and fully by brush to dry, previously unwashed shoulder-length hair from the roots to the ends. The fine temple hair received only a thin coating of the paste. It was important to ensure that all the hair was thoroughly coated with the hair coloring paste. The hair was then covered with a hood so that the hood closely followed the contours and was fixed in such a way that it could not slip. The paste applied was left on the hair thus covered for 30 minutes in the presence of heat (ca. 40° C.). After this contact time, the hood was removed and the hair coloring paste was thoroughly washed out with tap water (30° C.). The hair was then shampooed and rinsed until the hair and skin were completely clean.

2. Formulation Examples
2.1 Powder-form Hair Colorant
0.10 kg resorcinol
0.10 kg 1-hydroxy-3-aminobenzene
0.15 kg 2-amino-3-hydroxypyridine
0.10 kg 4-hydroxypropylamino-3-nitrophenol
0.15 kg HC Yellow No. 12
0.35 kg 2-methyl resorcinol
1.20 kg 2,5-diaminotoluene sulfate
1.00 kg indigo
2.00 kg walnjt shells
4.00 kg henna red
54.85 kg henna neutral
23.00 kg sodium perborate
5.00 kg carboxymethyl cellulose 92.00 kg of the above mixture were stirred in a mixer (for example a Lödige mixer) and then sprayed with 8.00 kg of paraffin oil (35 mPa·s, as measured at 2° C.).

40 g of the hair colorant were thoroughly mixed with 160 g of warm water (40° C.–50° C.) to form a readily spreadable paste. The resulting mixture—applied with a brush—was left to act on 50% grey, light brown hair for 30 minutes at 40° C. The paste was then rinsed off and the hair was shampooed and dried. The 50% grey, light brown starting hair had assumed a uniform light mocha-brown color.

2.2 Powder-forn Hair Colorant
0.15 kg resorcinol
0.10 kg 1-hydroxy-3-aminobenzene
0.15 kg 2-amino-3-hydroxypyridine
0.15 kg 4-hydroxypropylamino-3-nitrophenol
0.10kg HC Yellow No.12
0.30 kg 2-methyl resorcinol
1.25 kg 2,5-diaminotoluene sulfonate
1.00 kg camomile
1.50kg henna black
2.50 kg henna red
60.80 kg henna neutral
20.00 kg sodium perborate
5.00 kg carboxymethyl cellulose 93.00 kg of the above mixture were stirred in a mixer (for example a Lödige mixer) and then sprayed with 7.00 kg of paraffin oil (15 mPa·s, as measured at 2° C.).

40 g of the hair colorant were thoroughly mixed with 160 g of warm water (40° C.–50° C.) to obtain a readily spreadable application mixture. This mixture—applied with a brush—was allowed to act on 50% grey, dark blond hair for 30 minutes at 40° C. The application mixture was then rinsed off and the hair was shampooed and dried. The 50% grey, dark blond starting hair had assumed a uniform light chestnut color after the treatment.

2.3. Powder-form Hair Colorant
0.30 kg resorminol
0.10 kg 1-hydroxy-3-aminobenzene
0.15 kg 2-amino-3-hydroxypyridine
0.15 kg HC Yellow No. 12
0.45 kg 2-methyl resorcinol
2.00 kg 2,5-diaminotoluene sulfate
1.50 kg camomile
2.00 kg black alder bark
3.50 kg henna red
52.85 kg henna neutral
22.00 kg sodium perborate
5.00 kg carboxymethyl cellulose 90.00 kg of the above mixture were stirred in a mixer (for example a Lödige mixer) and then sprayed with 10.00 kg of caprylic/capric acid triglyceride.

40 g of the hair colorant were thoroughly mixed with 160 g of warm water (40° C.–50° C.) to obtain a readily spreadable paste. This mixture—applied with a brush—was allowed to act on 50% grey, mid-brown hair for 30 minutes at 40° C. The paste was then rinsed off and the hair was shampooed and dried. The 50% grey, mid-brown starting hair had assumed a uniform dark mocha brown color after the treatment.

3.4. Powder-form Hair Colorant
0.35 kg resorcinol
0.10 kg 1-hydroxy-3-aminobenzene
0.25 kg 2-amino-3-hydroxypyridine
0.30 kg 4-hydroxypropylamino-3-nitrophenol
0.10 kg HC Yellow No.12
0.45 kg 2-methyl resorcinol
2.25 kg 2,5-diaminotoluene sulfate
1.00 kg logwood
1.00 kg indigo
1.00 kg walnut shells
57.20 kg henna neutral
22.00 kg sodium perborate
5.00 kg carboxymethyl cellulose 91.00 kg of the above mixture were stirred in a mixer (for example a Lödige mixer) and then sprayed with 9.00 kg of octyl dodecanol.

40 g of the hair colorant were thoroughly mixed with 160 g of warm water (40° C.–50° C.) to obtain a readily spreadable paste. This mixture—applied with a brush—was allowed to act on 50% grey, light brown hair for 30 minutes at 40° C. The paste was then rinsed off and the hair was shampooed and dried. The 50% grey, light brown starting hair had assumed a uniform dark chestnut color after the treatment.

3.5. Powder-form Hair Colorant
0.20 kg rescrcinol
0.15 kg 1-hydroxy-3-aminobenzene
0.01 kg 4-hydroxypropylamino-3-nitrophenol
0.05 kg 2-amino-6-chloro-4-nitrophenol
0.40 kg 2-methyl resorcinol
0.90 kg 2,5-diaminotoluene sulfate
1.50 kg logwood
1.00 kg camomile
6.00 kg henna red
56.29 kg henna neutral
21.00 kg sodium perborate
5.00 kg carboxymethyl cellulose 92.50 kg of the above mixture were stirred in a mixer (for example a Lödige mixer) and then sprayed with 7.50 kg of dimethyl polysiloxane.

40 g of the hair colorant were thoroughly mixed with 160 g of warm water (40° C.–50° C.) to obtain a readily spreadable paste. This mixture—applied with a brush—was allowed to act on 80% grey, mid-blond hair for 30 minutes at 40° C. The paste was then rinsed off and the hair was shampooed and dried. The 80% grey, mid-blond starting hair had assumed a uniform mid-blond color after the treatment.

3.6. Powder-form Hair Colorant
0.01 kg resorcinol
0.10 kg 1-hydroxy-3-aminobenzene
0.15 kg 2-amino-3-hydroxypyridine
0.10 kg 4-hydroxypropylamino-3-nitrophenol
0.15 kg HC Yellow No.12
0.35 kg 2-methyl resorcinol
1.20 kg 2,5-diaminotoluene sulfate
61.85 kg henna neutral
23.00 kg sodium perborate
5.00 kg carboxymethyl cellulose 92.00 kg of the above mixture were stirred in a mixer (for example a Lödige mixer) and then sprayed with 8.00 kg of paraffin oil (35 mPa·s, as measured at 20° C.).

40 g of the hair colorant were thoroughly mixed with 160 g of warm water (40° C.–50° C.) to obtain a readily spreadable paste. This mixture—applied with a brush—was allowed to act on 50% grey, light brown hair for 30 minutes at 40° C. The paste was then rinsed off and the hair was shampooed and dried. The 50% grey, light brown starting hair had assumed a uniform light tobacco brown color after the treatment.

3.7 Powder-form Hair Colorant
0.15 kg resorcinol
0.10 kg 1-hydroxy-3-aminobenzene
0.15 kg 2-amino-3-hydroxypyridine
0.15 kg 4-hydroxypropylamino-3-nitrophenol
0.10 kg HC Yellow No. 12
0.30 kg 2-methyl resorcinol
1.25 kg 2,5-diaminotoluene sulfate
65.80 kg henna neutral
20.00 kg sodium perborate
5.00 kg carboxymethyl cellulose 93.00 kg of the above mixture were stirred in a mixer (for example a Lödige mixer) and then sprayed with 7.00 kg of paraffin oil (15 mPa·s, as measured at 20° C.).

40 g of the hair colorant were thoroughly mixed with 160 g of warm water (40° C.–50° C.) to obtain a readily spreadable paste. This mixture—applied with a brush—was allowed to act on 50% grey, mid-blond hair for 30 minutes at 40° C. The paste was then rinsed off and the hair was shampooed and dried. The 50% grey, mid-blond starting hair had assumed a uniform chestnut color after the treatment.

3.8. Powder-form Hair Colorant
0.30 kg resorcinol
0.10 kg 1-hydroxy-3-aminobenzene
0.15 kg 2-amino-3-hydroxypyridine
0.15 kg HC Yellow No. 12
0.45 kg 2-methyl resorcinol
2.00 kg 2,5-diaminotoluene sulfate
59.85 kg henna neutral
22.00 kg sodium perborate
5.00 kg carboxymethyl cellulose 90.00 kg of the above mixture were stirred in a mixer (for example a Lödige mixer) and then sprayed with 10.00 kg of caprylic/capric acid triglyceride.

40 g of the hair colorant were thoroughly mixed with 160 g of warm water (40° C.–50° C.) to obtain a readily spreadable paste. This mixture—applied with a brush—was allowed to act on 50% grey, mid-brown hair for 30 minutes at 40° C. The paste was then rinsed off and the hair was shampooed and dried. The 50% grey, mid-brown starting hair had assumed a uniform dark cocoa color after the treatment.

3.9. Powder-form Hair Colorant
0.50 kg resorcinol
0.20 kg 1-hydroxy-3-aminobenzene
0.10 kg 2-amino-3-hydroxypyridine
0.45 kg 2-methyl resorcinol
2.25 kg 2,5-diaminotoluene sulfate
60.50 kg henna neutral
22.00 kg sodium perborate
5.00 kg carboxymethyl cellulose 91.00 kg of the above mixture were stirred in a mixer (for example a Lödige mixer) and then sprayed with 9.00 kg of octyl dodecanol.

40 g of the hair colorant were thoroughly mixed with 160 g of warm water (40° C.–50° C.) to obtain a readily spreadable paste. This mixture—applied with a brush—was allowed to act on 50% grey, light brown hair for 30 minutes at 40° C. The paste was then rinsed off and the hair was shampooed and dried. The 50% grey, light brown starting hair had assumed a uniform mid-brown color after the treatment.

3.10 Powder-form Hair Colorant
0.20 kg resorcinol
0.15 kg 1-hydroxy-3-aminobenzene
0.01 kg 4-hydroxypropylamino-3-nitrophenol
0.05 kg 2-amino-6-chloro-4-nitrophenol
0.40 kg 2-methyl resorcinol
0.90 kg 2,5-diaminotoluene sulfate
64.79 kg henna neutral
21.00 kg sodium perborate
5.00 kg carboxymethyl cellulose 92.50 kg of the above mixture were stirred in a mixer (for example a Lödige mixer) and then sprayed with 7.50 kg of dimethyl polysiloxane 40 g of the hair colorant were thoroughly mixed with 160 g of warm water (40° C.–50° C.) to obtain a readily spreadable paste. This mixture—applied with a brush—was allowed to act on 80% grey, light blond hair for 30 minutes at 40° C. The paste was then rinsed off and the hair was shampooed and dried. The 80% grey, light blond starting hair had assumed a uniform mid-blond color after the treatment.

Solid hair colorants in powder or granular form containing at least one oxidation dye precursor, an oxidizing agent and typical additives, which additionally contain at least one substantive plant dye or henna neutral, are distinguished by excellent coloring results with complete covering of grey and no hair damage. The colorants are applied to the hair in the form of application mixtures prepared by mixing the powder or granules with water.

What is claimed is:

1. A solid hair colorant composition in powder or granular form, said colorant composition comprising from 1 to 10% by weight of at least one oxidation dye precursor, from 10 to 35% by weight of an oxidizing agent, from 3 to 25% by weight of a substantive plant dye or 25 to 70% by weight of henna neutral, and optionally conventional cosmetic additives, based on the weight of said solid hair colorant composition.

2. A hair colorant composition as in claim 1 wherein said oxidation dye precursor comprises at least one primary intermediate and at least one secondary intermediate dye precursor.

3. A hair colorant composition as in claim 2 wherein said primary intermediate dye precursor is selected from the group consisting of p-phenylenediamine, p-toluylenediamine, 2-(2-hydroxyethyl)-1,4-diaminobenzene, p-aminophenol, 3-methyl-4-aminophenol, 2,4,5,6-tetraaminopyrimidine and 2-hydroxy-4,5,6-triaminopyrimidine.

4. A hair colorant composition as in claim 2 wherein said secondary intermediate dye precursor is selected from the group consisting of -naphthol, resorcinol, 4-chlororesorcinol, 2-methyl resorcinol, m-aminophenol, m-phenylenediamine, m-toluylenediamine, 1,5- or 1,7-dihydroxynaphthalene, 5-amino-2-methylphenol, and 6-amino-2-methylphenol.

5. A hair colorant composition as in claim 1 wherein said oxidizing agent is selected from the group consisting of an addition compound of hydrogen peroxide with urea, melamine, potassium perborate, sodium perborate or ammonium peroxodisulfate, and mixtures thereof.

6. A hair colorant composition as in claim 1 further containing a synthetic substantive dye.

7. A hair colorant composition as in claim 6 wherein said synthetic substantive dye is selected from the group consisting of 4-hydroxypropylamino-3-nitrophenol, HC Red No. 3, N,N'-bis-(2-hydroxyethyl)-2-nitro-p-phenylenediamine, HC Blue No. 2, HC Yellow No. 2, HC Yellow No. 12, HC Blue No. 12, and 2-amino-6-chloro-4-nitrophenol.

8. A hair colorant composition as in claim 1 further containing 1 to 30% by weight of an inert organic compound having a melting point below 50° C., based on the weight of said hair colorant composition.

9. A hair colorant composition as in claim 8 wherein said inert organic compound is selected from paraffin oil, triglycerides, fatty alcohols and polysiloxanes.

10. A hair coloring application composition containing a mixture comprising 15 to 25% by weight of a hair colorant composition comprising from 1 to 10% by weight of at least one oxidation dye precursor, from 10 to 35% by weight of an oxidizing agent, from 3 to 25% by weight of a substantive plant dye or 25 to 70% by weight of henna neutral, and optionally conventional cosmetic additives, based on the weight of said hair colorant composition, and 75 to 85% by weight of water, based on the weight of said application composition.

11. A hair coloring application composition as in claim 10 having a pH of 5 to 12.

12. A process for preparing a solid hair colorant composition in powder or granular form comprising mixing from 1 to 10% by weight of at least one oxidation dye precursor, from 10 to 35% by weight of an oxidizing agent, from 3 to 25% by weight of a substantive plant dye or 25 to 70% by weight of henna neutral, and optionally conventional cosmetic additives, based on the weight of said solid hair colorant composition, and then adding to said solid hair colorant composition from 1 to 30% by weight of an inert organic compound having a melting point below 50° C., based on the weight of said hair colorant composition.

* * * * *

UNITED STATES PATENT AND TRADEMARK OFFICE
CERTIFICATE OF CORRECTION

PATENT NO.    : 6,139,853
DATED         : October 31, 2000
INVENTOR(S)   : Akram et al.

It is certified that error appears in the above-identified patent and that said Letters Patent is hereby corrected as shown below:

Column 8,
Line 54, delete "-naphthol", and insert therefor -- α-naphthol --.

Signed and Sealed this

Twenty-first Day of October, 2003

JAMES E. ROGAN
*Director of the United States Patent and Trademark Office*